US008348666B2

(12) United States Patent
Beck (10) Patent No.: US 8,348,666 B2
(45) Date of Patent: Jan. 8, 2013

(54) DYNAMIC WATER SPRAY INTENSITY FOR DENTAL HANDPIECES

(75) Inventor: Timothy M. Beck, York Haven, PA (US)

(73) Assignee: Dentsply International, Inc., York, PA (US)

( * ) Notice: Subject to any disclaimer, the term of this patent is extended or adjusted under 35 U.S.C. 154(b) by 1435 days.

(21) Appl. No.: 11/673,830

(22) Filed: Feb. 12, 2007

(65) Prior Publication Data

US 2008/0193893 A1 Aug. 14, 2008

(51) Int. Cl.
A61C 1/00 (2006.01)

(52) U.S. Cl. .......................................................... 433/27

(58) Field of Classification Search ............ 433/27, 433/132, 128, 82, 84, 95
See application file for complete search history.

(56) References Cited

U.S. PATENT DOCUMENTS

| | | | | |
|---|---|---|---|---|
| 3,959,883 A | * | 6/1976 | Walls et al. ................. | 433/98 |
| 5,476,380 A | * | 12/1995 | Rosenstatter ................. | 433/100 |
| 6,186,784 B1 | * | 2/2001 | Bailey ................. | 433/126 |
| 2006/0063127 A1 | * | 3/2006 | Gugel et al. ................. | 433/82 |
| 2006/0290200 A1 | * | 12/2006 | Davison et al. ................. | 303/138 |

* cited by examiner

Primary Examiner — Sunil K Singh
(74) Attorney, Agent, or Firm — McNees Wallace & Nurick LLC (57) ABSTRACT

A water spray intensity system for providing water to a dental workpiece based on dynamic conditions experienced by the handpiece. The dental workpiece is a dental structure, typically in the mouth of a patient. A periodic function of the handpiece may include a motion such as a periodic motion of a tool of the handpiece, the speed of the rotating tip or some measurable parameter such as the torque experienced by a rotating tip assembled to the handpiece. Instead of providing water at a constant flow rate, the periodic function of the handpiece, such as torque or tip speed, is made by measuring a parameter associated with the handpiece. The water spray intensity system then automatically adjusts the flow of water from the handpiece based on the sensed parameter or periodic function to improve cutting efficiency.

69 Claims, 5 Drawing Sheets

DYNAMIC WATER SPRAY INTENSITY FOR DENTAL HANDPIECES

FIELD OF THE INVENTION

The present invention is directed to dental handpieces having adjustable water spray intensities and specifically to dental handpieces having water spray intensities that are automatically adjusted based on speed of the tool or load experienced by the tool.

BACKGROUND OF THE INVENTION

Most dental handpieces provide a supply of water and air that can be impinged on a workpiece, typically a tooth or other dental structure. The water and air are provided so as to impinge on the workpiece. This air is referred to as chip air and is to be distinguished from air that is used to power a particular type of dental handpiece, a pneumatic handpiece, that relies on a separate supply of air to power an air turbine that rotates the cutting instrument affixed to a distal end of the dental handpiece.

Figure 1:
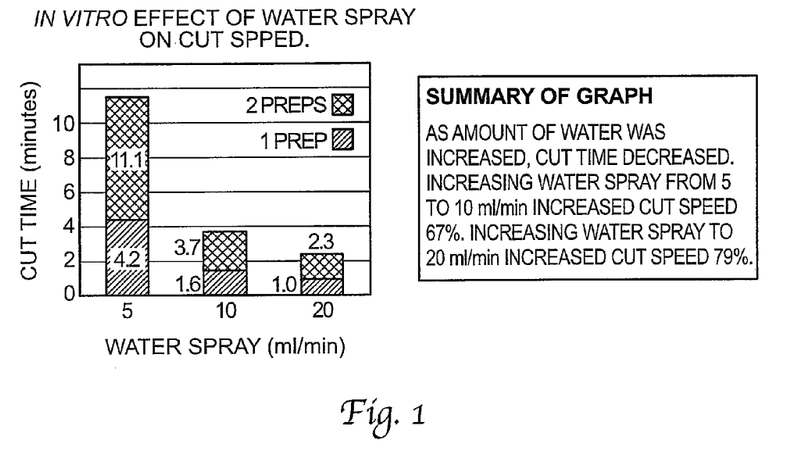
FIG. 1 is a prior art graphical representation of the contribution of increased amounts of water to cutting time during a dental procedure.

It is known in the art that increasing the flow of water improves the cutting ability at constant load of a tool affixed to the distal end of a handpiece, increases the cutting efficiency and decreases the cutting time of an operation. The water spray assists by keeping the workpiece, that is the tooth, cool. It also provides essential lubrication during the cutting operation. It further minimizes clogging of the tool itself, as the water flushed and carries away small particles that would otherwise become embedded in the surface of the tool, decreasing its cutting ability. These benefits were outlined in an article in CRA Newsletter Volume 25, Issue 9, September 2001, p. 2. FIG. 1 depicts the effects of varying the amount of coolant water to a dental workpiece. It is clear that increasing the amount of water decreased the cutting time.

There are tools currently available that let the dental professional physically increase the flow of water to the workpiece, if so desired by manual or foot adjustment. In many tools, this increased flow of water is provided even when the rate of cutting is reduced or diminished.

While an increased flow of water is generally desirable, there are problems associated with the increased flow of water. Specifically, water accumulation can occur in the oral cavity, even when suction for removal is provided. Furthermore, this excess water is provided even when not needed, such as when the dental professional is engaged in light cutting. The excessive water may ultimately result in the production of excessive spray that may occur when starting or backing off an operation, the excessive spray hindering visibility and impairing the ability of the dental professional in conducting a visual examination.

A dental handpiece that provides the benefits of improved water flow while overcoming the deficiencies is not available, but is much desired by dental professionals, and the present invention provides such a device.

SUMMARY OF THE INVENTION

The present invention is a dynamic water spray intensity system that provides water to a dental workpiece based on a periodic function of the handpiece. The dental workpiece is a dental structure, typically in the mouth of a patient. The periodic function of the handpiece may include a motion such as a periodic motion of a tool of the handpiece, the speed of the rotating tip or some measurable parameter such as the torque experienced by a rotating tip assembled to the handpiece. Instead of providing water at a constant flow rate, the present invention determines the periodic function of the handpiece, such as torque or tip speed measuring a parameter associated with the handpiece. The dynamic water spray intensity system then automatically adjusts the flow of water from the handpiece based on the sensed parameter or periodic function.

The dynamic water spray intensity system comprises a dental handpiece. As is conventional, the dental handpiece includes a proximal end, a distal end and a body extending between the proximal end and the distal end. The body usually is ergonomically designed for the comfort of the dental professional using the handpiece. A rotating tip is removably assembled to the distal end of the handpiece and extends away from the handpiece. The handpiece further includes a means for driving the rotating tip. A means for measuring a movement of the tip is also provided with the system. The movement of the tip may be related to a periodic function of the tip, so the means of measuring the movement can include a means for measuring a periodic function of the tip. A water line is positioned within the handpiece body, extending from the proximal end to the distal end. In addition, an air line is positioned within the handpiece body, extending from the proximal end to the distal end. This air line combines with water from the water line to provide a water spray in proximity to the rotating tip and directed at the dental workpiece at or near where the rotating tip contacts the dental workpiece. This air is referred to in the art as chip air and the air line is referred to as the chip air line.

The dynamic water spray intensity system further includes a water supply in communication with the water line in the handpiece body to provide a supply of water. A conduit extends between the water supply and is coupled to the water line in the handpiece body. An air supply is in communication with the chip air line in the handpiece body to provide a supply of air. In addition, a means for comparing the flow of water through the handpiece with the movement of the handpiece is provided. A means for regulating the flow of water through the handpiece to the workpiece based on the movement of the handpiece is also provided. This means for regulating allows for adjustment of the flow of water to the proper flow rate based on the measured movement of the handpiece.

The present invention further contemplates a means for measuring a periodic function of the handpiece indicative of a speed of the tool or tip as it is driven by the means for providing power. A means for comparing the flow of water with the measured speed of the tool is also provided. When the means for comparing the flow of water and the operational periodic function of the handpiece indicative of the speed of the tool indicates that the flow of water must be adjusted, the means for regulating the flow of water to the workpiece is adjusted to increase or decrease the flow or water consistent with the measured tool speed, the tool speed typically being a rotational speed of the tool or tip.

The means for driving the rotating tip may be pneumatic or electric. A chuck positioned at the distal end is used to removably secure the rotating tip. When the means for driving the rotating tip is pneumatic, the chuck is attached to a rotatable air turbine. In such a pneumatic handpiece, a second air line extends within the body from the proximal end of the body to the rotatable air turbine. The second air line is connected to a supply of pressurized air and provides air to drive the turbine, and an exhaust line carries this drive air away from the turbine. The supply of air to the second air line is regulated by a means for regulating. Such a pneumatic handpiece may also include a set of bearings to facilitate rotation of the chuck.

When the means for rotating the handpiece is electric, an electric motor is conventionally included in the body of the handpiece to drive the rotating tip, the electric motor typically being double insulated from the chuck, the bearings and the tip to prevent any possibility of an electric shock to the patient. The electric motor may be powered by an appropriate connection to an AC line, or by a battery included in the handpiece.

An advantage of the present invention is that the amount of water provided to the workpiece is based on a measured periodic movement of the tool. The amount of water provided to the workpiece can be proportional to this measured periodic movement of the tool so that patient comfort is maintained, cutting tool efficiency is improved and the workpiece is not needlessly obscured from the view of the dental professional.

Another advantage of the present invention is that the dental professional can rely on the system to provide the proper amount of water to both the dental workpiece and the tool. This can prevent the workpiece from overheating while also extending the life of the tool.

Still another advantage of the present invention is that the cutting efficiency of the handpiece and the tool can be improved by selecting the proper amount of water required based on the operation being performed This can result in the use of smaller devices having a lower power requirement. And by improving the cutting efficiency, the duty cycle of the spray system can be extended.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

The present invention provides a dynamic water spray intensity system in which the water spray intensity is determined and adjusted based on a measured periodic function of an instrument, such as a periodic movement of the instrument, the instrument being part of the system. The present invention is directed to a system that automatically adjusts the spray intensity directed at the workpiece based on a measured function of the tip or tool at the distal end of the handpiece by modifying the water flow. It will be recognized by those skilled in the art that the spray intensity may also be adjusted by simultaneously adjusting the flow of chip air in conjunction with the water flow in substantially the same way, and the present invention encompasses such chip air control.

The dynamic water spray intensity system comprises a handpiece, a supply of chip air connected to the handpiece and a supply of water connected to the handpiece. A means for regulating the supply of water is also provided. The handpiece has a proximal end, a distal end and a body extending between the proximal end and the distal end. The body is ergonomically designed so that it can be comfortably handled by the dental professional. A tip is removably assembled to the distal end of the handpiece and extends therefrom so that a dental operation can be accomplished on the mouth of a patient. The dental operation can be cleaning which utilizes a reciprocating or substantially linear or figure 8 type of motion, or may be a cutting operation, which conventionally involves rotation of a cutting tool. The removable cutting tool conventionally is a rotating tip, the removable tip being a bur, a rasp or a file or a drill bit. It typically is assembled into a chuck. The chuck conventionally is connected to a means for driving. The means for driving causes the chuck to rotate, which in turn causes the rotating tip to rotate. Typically the chuck is mounted on a set of ball bearings which promotes smooth rotation of the assembly consisting of the chuck, the bur and the ball bearings as they are rotated by the means for driving. The handpiece includes a means for measuring a periodic function of the handpiece. The dynamic water spray intensity system of the present invention also includes a means for comparing the flow of water through the handpiece with the measured periodic function of the handpiece. Although much of the discussion relates to a rotatable cutting tool, it will be recognized by those skilled in the art that a cleaning operation involves a linear movement, which also is periodic and the dynamic water spray intensity system can be utilized with such a system.

The tip typically extends from the distal end of the handpiece. The tip is a replaceable tool inserted into a chuck-type device on the distal end of the handpiece. The tool can be of varying configuration, depending upon the operation being performed by the dental professional. The handpiece and tool can be used for standard dental procedures such as teeth cleaning or cavity removal and repair, or can be used for specialized dental procedures such as periodontic operations. In all of these procedures, water can be supplied to the dental structure or workpiece.

Water flow rate during a dental procedure affects cutting efficiency. Heretofore, water was combined with chip air during a dental procedure to provide a water spray to the dental workpiece. The variation of the water spray has been by physical manipulation of the water flow by the dental professional during the procedure, such as by manual modification of water flow or through use of a foot pedal. The water is provided in the form of a spray to cool the dental workpiece, provide lubrication during cutting and carry away the chips, that is, the debris resulting from the cutting operation. This debris can clog the tool or bur and impair cutting. However, too much water in the form of a spray can impede the dental professional's ability to view the workpiece as the procedure proceeds, and can lead to patient discomfort as the water accumulates in the oral cavity. As used herein, the workpiece refers to the dental structure of a patient, although more generally, the workpiece may be a replica of a patient's dental structure.

The present invention automatically regulates the flow of water provided to the workpiece based on a measured function of the handpiece. For example, the flow of water is adjusted to provide maximum lubrication and cooling and to move debris from the worksite when a high rate of cutting is being performed by the tip at high speeds and low loads, and to minimize the flow of water to the workpiece when a low rate of cutting is being performed by the bur at low speeds and low loads. This improves visibility of the dental professional during the cutting, minimizes patient discomfort by reducing the accumulation of water in the oral cavity, yet does not adversely affect the cutting performance of the bur. The measured periodic function of the handpiece is an indication of the cutting rate. This function is measured by a means for measuring this periodic function, such as a sensor, in the handpiece. Based on this measured value, the flow of water is adjusted by the means for regulating the water supplied to the handpiece. As the measured periodic function indicates that cutting rate is increasing, or is high, the means for regulating the water supplied to the handpiece is adjusted to provide more water to the handpiece. As the measured periodic function indicates that the cutting rate is decreasing or is low, the means for regulating the water supplied to the handpiece is adjusted to provide less water to the handpiece. However, sufficient water is still provided so as to provide adequate cooling, lubrication and debris removal, while reducing the spray and water accumulation in the oral cavity. This is accomplished automatically and with no additional action by the dental professional.

A means for powering the rotating tip in the form of a replaceable tool is provided. Various means for powering the tip are available. A means for measuring the rotating speed of the tip is also provided. A supply of water is directed at the dental structure or workpiece. The supply of water directed at the dental structure flows from a water supply through a conduit in the handpiece body, combines with chip air at the distal end and is directed at the dental structure or workpiece positioned in proximity to the rotating tip. The means for providing power and a channel for water from the water supply conveniently pass through or are contained in the handpiece body.

Figure 2:
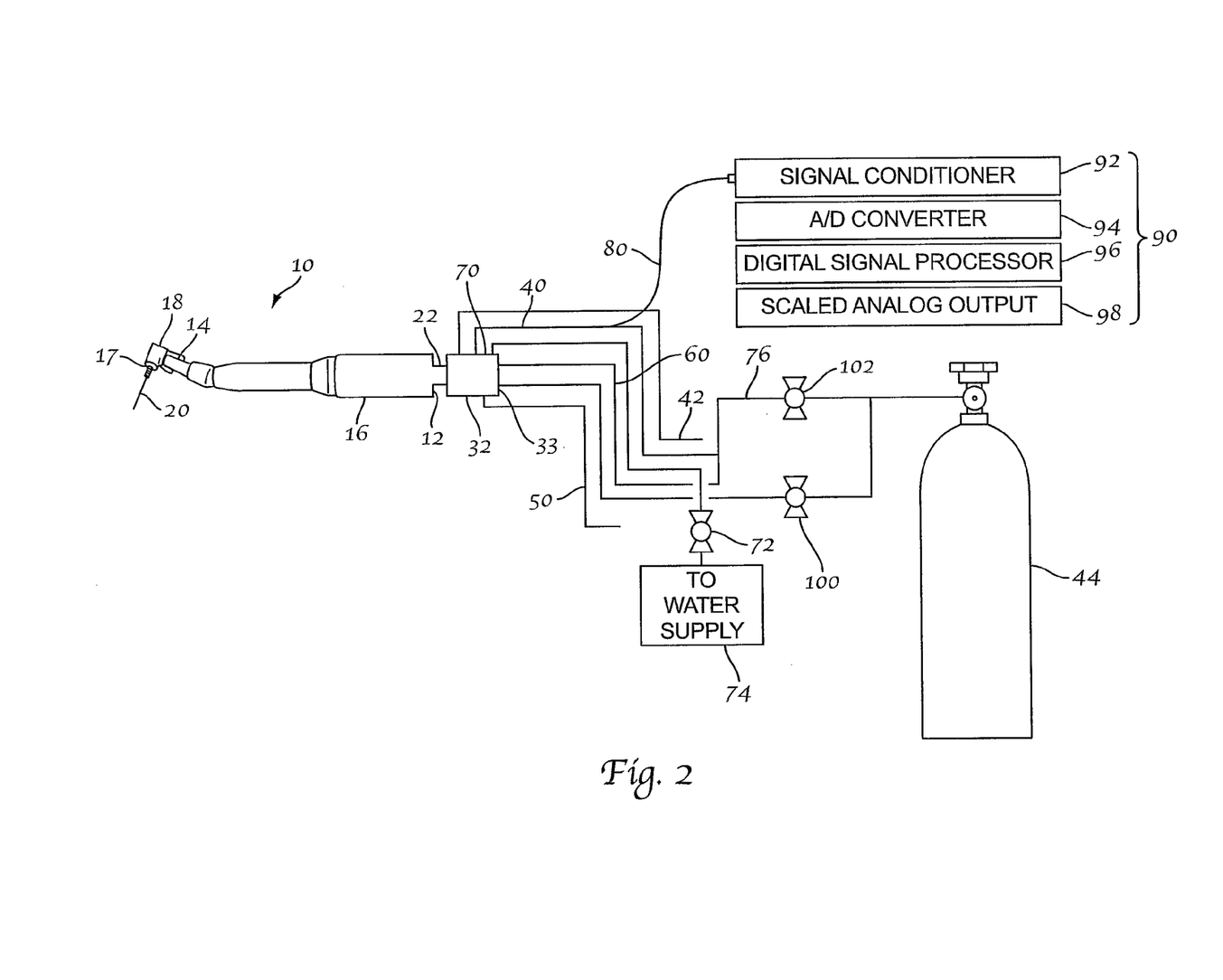
FIG. 2 depicts a first embodiment of the adjustable dynamic water spray intensity system for dental handpieces of the present invention powered by a pneumatic source.

FIG. 2 represent a first embodiment of the dynamic water spray intensity system 2 of the present invention, which is powered pneumatically. The system 2 includes a handpiece 10 having a proximal end 12, a distal end 14 and a body 16 extending between the proximal end 12 and distal end 14. A rotating turbine assembly 17 comprising a chuck 18, and bearings connected to an air turbine is located at the distal end 14. A bur 20 is assembled into the chuck 18, where it is mechanically secured, the bur extending in a direction away from the distal end to allow the dental professional to manipulate the handpiece during the dental procedure. Handpiece 10 further includes a first air line 52 and a water line 54 extending from the proximal end 12 to the distal end 14 of the handpiece. The first air line 52 provides chip air and combines with the water line at the distal end 14 of the handpiece to direct a water spray at bur, 20, which is the location of the dental workpiece when the handpiece is proximate the workpiece. The air turbine of the rotating turbine assembly 17 is driven pneumatically by pressurized air. This air is supplied by a second air line 56 that extends from the proximal end 12 of the handpiece to turbine assembly 17, the air being exhausted through the handpiece 10 by an exhaust line 50 extending from the turbine assembly back toward the proximal end of the handpiece.

First air line 52 that provides chip air is connected to the air supply 44 via a first air conduit 76. Second air line 56, the means for driving the rotating tip, is connected to the air supply via a second air conduit 60. The conduits are connected to the lines via a coupler, which is well-known, the coupler further facilitating connection of the water supply 74 to water line 54 in handpiece 10 via water conduit 75, the flow of water being controlled by regulator 72, which can be a proportionally controlled valve. A separate regulator for regulating the amount of air flowing through each of these lines is provided so that the air flow in the lines can be separately controlled. These regulators can be controlled simply, such as proportionally controlled valves 72, 100, 102, as shown, can be controlled by equipment designed to carefully meter the flow of fluid provided to the lines or can be controlled by simple valves. These conduits are depicted in FIG. 2 as part of a pneumatic supply hose 40 that conveniently is assembled to the handpiece via mating hose coupling 32 and handpiece coupling 22.

FIG. 2 further includes a means for detecting a mechanical function 70. As used herein, a mechanical function is any periodic mechanical artifact that is generated by operation of the handpiece 10. A mechanical artifact includes but is not limited to any periodic mechanical vibration of the handpiece, a pressure, an acoustic wave or an oscillation resulting from its operation. The means for detecting are sensors that may also include an electrical or a magnetic speed detection means, or combination of electrical and mechanical speed detection means in the handpiece that provides an indication of the rotational speed of the bur or turbine in a periodic fashion. In a preferred embodiment, the mechanical function detected is the periodic vibration of the rotating tool transmitted through the handpiece, such as a vibration of the bearings of the rotating turbine assembly and preferred means for detecting this mechanical function is an accelerometer. However, depending upon the mechanical function monitored, the means for detecting may vary. The means for detecting can include a pressure transducer, a sound transducer, a linear variable differential transformer (LVDT), a microphone or an acoustic device for detecting acoustic transmissions from operation of the handpiece. A pressure transducer may be used to detect the mean pressure in the handpiece. Alternatively, the pressure transducer may be used to detect the difference in pressure between the inlet and outlet pressure or to detect pressure pulsations. The means for detecting may also be any means (optical or other) for detecting periodic vibrations in the handpiece, since such vibrations are indicative of the tool tip rotational speed. The means for detecting may also be an optical speed detection means such as an optical encoder to detect an optical signal from an optical signal generator associated with the rotating tool. The means for detection may also be a Hall Effect-type encoder that uses magnetic and electrical impulses to determine rotational speed. In a Hall Effect device, a rotating magnet generates an electrical field, which field can then be detected. The sensor 70 can be located at any location where an accurate determination of the periodic function can be obtained. The handpiece 10, the pneumatic supply line 40 and the coupler between the handpiece 10 and pneumatic supply line 40 are possible locations. However, when located in the handpiece 10, the sensor should be sealed so that sterilization can be accomplished without damaging the sensor. The sensor may be unsealed if it is resistant to degradation due to exposure to the fluids and temperatures used in the required sterilization procedures.

The sensor 70 is in communication with a means for comparing the flow or water through the handpiece 10 with the detected periodic function of the tip, a controller 90. In the embodiment of FIG. 2, the sensor 70 detects the rotating speed of the tip and transmits it to the controller 90. Although sensor 70 is depicted as wired to controller 90 by means of embedded sensor wire leads 80, as shown in the accompanying FIG. 2, the present invention contemplates wireless communication between the sensor 70 and the controller 90, such as by transmission of RF signals as is well known. The water flow from the water supply is also controlled by the controller.

This can be by use of a solenoid valve or by regulator. The solenoid valve or regulator can be calibrated to provide flow information, such as by use of a calibrated variable flow valve. Alternatively, flow rate from the water supply can be controlled by a mass flow meter. In yet another embodiment, a flow sensor can provide flow information to the controller, and the controller can then signal the valve or regulator to adjust the flow based on the sensor readings.

The controller compares the rotating speed of the bur or tip 20 to the flow of water provided to the handpiece. This amount of water can be provided to the controller from the proportionally controlled water valve 72 which is also in communication with the controller. The controller can be programmed with an algorithm that compares the measured rotating speed of the tip with the flow of water to the handpiece. Alternatively, the controller may have a predetermined look-up table that specifies the required flow of water based on a measured rotating speed. When the required flow of water and the measured rotating speed are proper, no action is taken by the controller. When the required flow of water deviates from the measured rotating speed of the tip 20, the controller signals the proportionally controlled water valve or mass flow meter to modify the flow of water to the handpiece appropriately, based on the measured rotating speed of the tip. The controller may be any programmable device such as a programmable computer or microprocessor, or it may be a non-programmable dedicated device capable of accomplishing the above actions.

Figure 3:
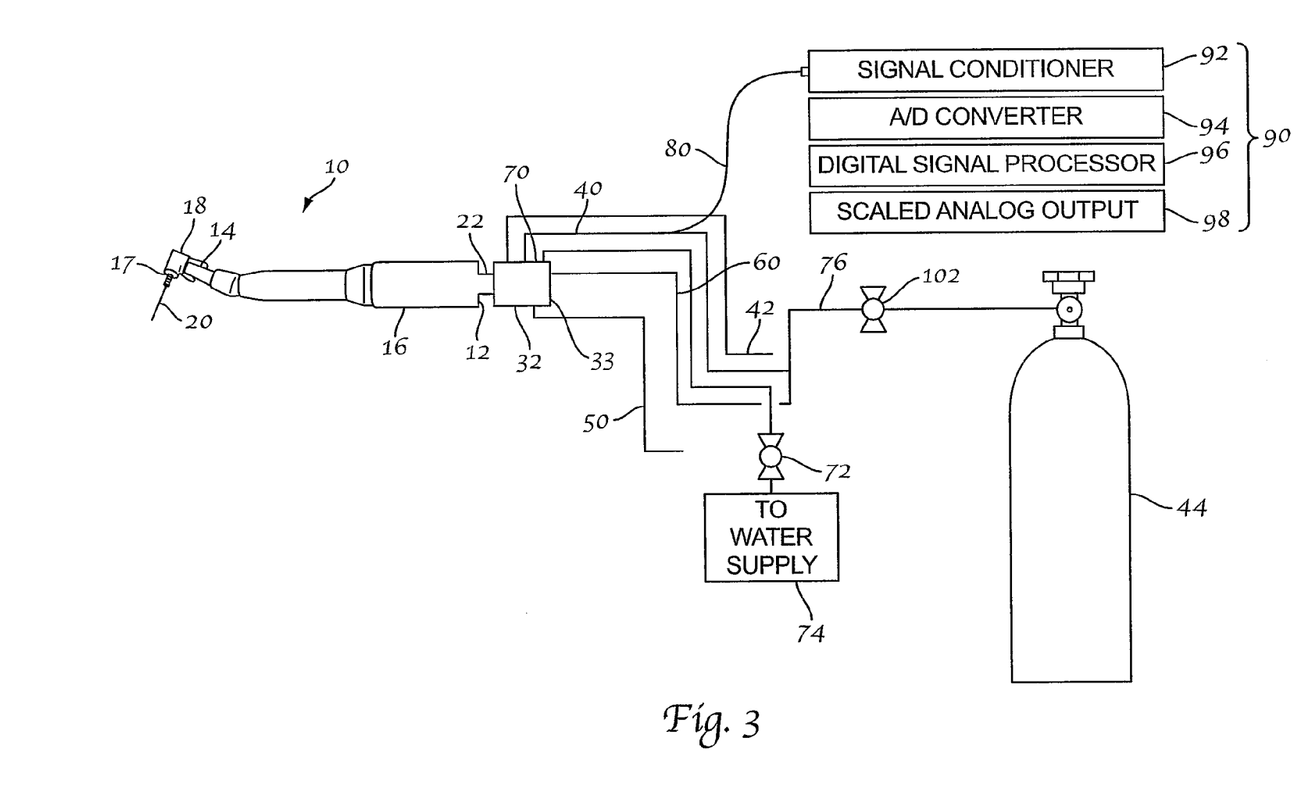
FIG. 3 depicts a second embodiment of the adjustable dynamic water spray intensity system for dental handpieces of the present invention powered by an electric motor.

FIG. 3 depicts a second embodiment of the adjustable dynamic water spray intensity system of the present invention. This embodiment is substantially the same as the embodiment shown in FIG. 2, but power is supplied by an electric motor 104 rather than by an air supply. While distinct differences exist operationally between an electric handpiece and a pneumatic handpiece, the differences are not significant to the operation of this invention, except as noted herein. Of course, the electric handpiece itself must either include a power source, batteries, or include connections to a power source, electrical wiring, although a second air line and an exhaust line are not required for an electric handpiece. The electric motor provides the power to drive the handpiece. The means for detecting a mechanical function of the rotating tip is a sensor 70, preferably an accelerometer, which provides feedback to controller 90 related to the rotational speed of the tip. The accelerometer may be located in the handpiece or in the coupler as previously discussed. Alternatively, the rotating speed of the tip can be related to the current drawn by the motor. This current can be measured at the power supply by an appropriate meter and provided to the controller for determination of tip speed. The relationship between water flow and rotational speed of the handpiece is as identified in the first embodiment of the present invention.

The controller 90 is an important component of the present invention. The controller can be a simple microprocessor or other electronic device capable of executing functions and communicating with equipment required for operation of the present invention. Communications typically is by signals, either through direct connection or by RF. The controller 90 can either receive analog signals and convert them to digital signals, or can receive digital signals from the equipment with which it must communicate. In a similar fashion, the controller 90 can send analog signals or digital signals, depending on the input required by the equipment receiving signals from the controller. The controller 90 can receive signals indicative of the various conditions in the dynamic water spray intensity system of the present invention, enabling the flow of water to be controlled. The controller can also store and execute algorithms that provide the relationship between a measured condition of the tip, such as rotational speed or torque encountered by the bur or tip 20 and water flow. The algorithms can be complex mathematic relations that precisely calculate the relationship between water flow and tip speed or simple mathematical tables (look-up tables) that stipulate required flow ranges corresponding to tip condition ranges. The controller can also signal the means for controlling the water flow to increase or decrease the water flow based on the execution of the stored algorithms. When the system includes a sensor for measuring the flow of water, the controller can be set up to include a feed-back loop to ascertain that the measured flow of water is consistent with the flow of water from the water supply and the required flow of water based on the measured condition of the tip. The controller also includes the ability to signal water control means such as a variable flow valve, a solenoid valve controlling water flow or a more complex mass flow meter that more precisely controls water flow, these means for controlling water flow being responsive to signals from the controller. In a more complex arrangement, the controller can also be arranged to control the flow of chip air so that the chip air component to dynamic water spray intensity can also be modified either directly based on the water flow or based on the measured condition of the tip. Additional algorithms or look-up tables are required so that the controller can establish the relationship between chip air flow and either water flow or the measured condition of the tip. Of course, the system itself must include means to regulate chip air flow, and communications means between the controller and chip air flow regulator to regulate the chip air flow. This means for regulating chip air flow can be as simple as a solenoid valve or flow regulator operable based on a signal from the controller, or a more costly mass flow meter. The controller can also include an algorithm to decide which function experienced by the handpiece should control the flow of water to the workpiece, such as, for example, whether the flow of water through the handpiece and to the workpiece should be determined and controlled by the speed of the operating tip or by the torque encountered by the operating tip. While description of the operation of this controller are novel and uniquely identified for this invention, the operation and design of such a controller as disclosed herein should be within the skill of a routiner in the art of controllers armed with the knowledge of this invention.

A means for determining a function of the tip 70 is also an important aspect of the present invention. The flow of water in the water line is ultimately dependent on an accurate measurement of this function, whether indicative of tip speed, torque encountered by the tip, power or some other function relative to cutting, and the transmittal of a signal indicative of this function to the controller. In its broadest embodiment, the means for determining the function of the tip measures an important function of the tip, and the measuring of this function must be communicated to the controller. Thus, if the speed of the tip is the function that is important, the sensor must be capable of accurately measuring the speed of the tip and communicating that speed to the controller 90. In this circumstance, the sensor 70 can be an accelerometer that measures a periodic vibration of a moving part in the handpiece. Usually, such a vibration is associated with the bearings, but is not so limited. Alternatively, the sensor 70 can be a microphone, either located within the handpiece 10, or may be located external to but in proximity to the handpiece. Again, the microphone picks up a periodic sound associated with the motion of the tip.

Alternatively, the means for determining the function of the tip can measure resistance of the tip to rotation, such as occurs when the torque encountered by the tip increases. For an electric motor, this increase in torque can be related to the increase in current required by the motor to rotate the motor. Thus, an ammeter at the power supply can accurately determine this current and communicate this measured value to the controller, and the controller can thus determine the torque encountered by the rotating piece. Alternatively, but somewhat related, the power supplied to the tip can be related to the water flow requirements for the tip. Thus a motor-related power setting or power drawn by the motor may also be used. Torque can also be estimated in a pneumatic hand piece. An air supply at a substantially constant, preselected pressure provides the power to drive the rotating tip. This pressure can be communicated to the controller. The controller can determine the torque encountered by the rotating tip as a function of this preselected air pressure and the speed of the rotating tip, based on an algorithm or approximate the encountered torque with a look-up table. At low torque values, a low flow of water is required, so visibility to the dental professional is good. However, as torque increases, an increased flow of water is required to keep the workpiece cool, increase lubrication, remove debris from the work area and keep the tip or burr from clogging.

Fluid control devices are also an important aspect of the present invention. The ability of the fluid control devices to accurately control the flow of water in or to the handpiece is necessary to provide a proper flow of water to the workpiece. A proper fluid control device must be capable of increasing or decreasing the flow of fluid in response to a signal from the controller. The communication of the signal may be via RF signal or by a direct connection to the controller. One type of fluid control device accurately meters the flow of fluid. These can include calibrated solenoid valves or calibrated proportionally controlled valves. Another more expensive fluid control device may be a simple valve used in conjunction with a mass flow meter, the mass flow meter in communication with the controller. The mass flow meter can be a complex device having a microprocessor that itself may be a controller 90 that receives the signals from the means for determining the function of the tip 70 and responds directly to the received signal or it may be a separate piece of equipment that is in communication with a controller. Mass flow meters provide very precise metering of fluids. A fluid control device is used to control the water flow and may be included in the handpiece 10 to control water flow in water line 54, in the coupler to the handpiece or in the line from the water supply to the coupler. A fluid control device may also be used to control chip air flow in chip air line 52, in the coupler to the handpiece or in the line from the air supply to the handpiece. The chip air flow can be controlled, as discussed above, when the adjustable dynamic water spray intensity system is configured to control chip air flow in conjunction with water flow. A fluid control device is also used in pneumatic systems to control the flow of drive air in second air line 56 (FIG. 2) used to power the air turbine. In this embodiment, the air used to power the air turbine can be a variable function, as determined by the dental professional based on the dental procedure being performed. An accurate determination of the air flow used to power the turbine can be used to determine the amount of water flow required to provide cooling for a dental procedure.

Optional measuring devices include flow measurement devices in the fluid flow lines. These optional flow measurement devices provide accurate determinations of actual flow conditions in a conduit and line. These flow measurement devices are generally simple sensors designed to communicate real time information of flow conditions to the controller either by direct connection or by RF (radio frequency). Although simple devices, these sensors can be used in conjunction with the controller and with the previously described fluid control devices to form a feedback loop that quickly and accurately controls the flow of water in or to the water line 54, the flow of chip air in or to the chip air line 52 and/or the flow of drive air in or to the second air line 56 to drive the air turbine for pneumatic handpieces.

Figure 4:
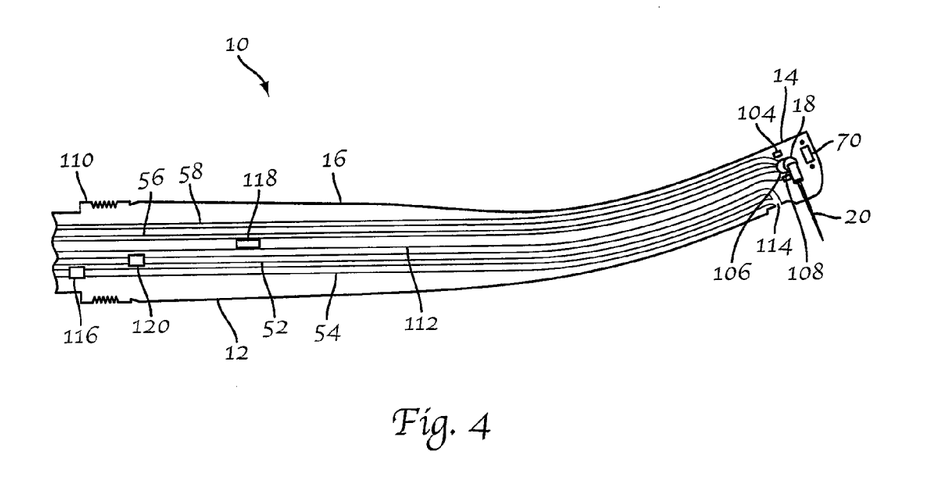
FIG. 4 depicts a detailed schematic illustration of a preferred handpiece or the present invention.

A preferred embodiment of the handpiece 10 of the present invention is shown in more detail in the enlarged cross-section of FIG. 4. The handpiece 10 includes a proximal end 12, a distal end 14 and a body 16 extending between the proximal end 12 and the distal end 14. A threaded connection 110 is assembled at the proximal end for assembly to a coupling. A rotating tip 20 or bur is assembled to the distal end 14 of the handpiece. Chip air is provided through chip air line 52 and water is provided through water line 54, which combine at orifice 114 to direct a water spray at a workpiece, not shown, whose location is at the end of tip 20. A means for rotating the tip is provided. For a pneumatic handpiece, this means for rotating is an optional air turbine 106 attached to bearings 108, the air turbine powered to rotate the bearings, the bearings 108, the chuck 18 and tip 20 constituting the rotating assembly 17. The means for rotating also includes drive air supplied by second air line 56 or drive air line and exhaust air 58 provided by exhaust air line 58, these lines being mandatory only in a pneumatic handpiece. For a handpiece powered by an electric motor, the means for rotating is optional electric motor 104. Wires 112 for connecting the electric motor 104 to an external power source are depicted, although those skilled in the art will recognize that the power source may be batteries, preferably rechargeable, positioned within the body. In this embodiment, a means for measuring the periodic function of the tip 20, preferably a sensor 70, is positioned in the body 16. The sensor 70 may be a microphone, which can measure a periodic sound. More preferably, the sensor is an accelerometer that is tuned to detect a periodic vibration of the rotating assembly, such as a vibration given off by the bearings. The means for measuring a periodic function can be more complex, and can include an optical encoder or a Hall Effect encoder included in the rotating assembly for precisely measuring the rotational speed of the assembly 17. Whatever sensor is selected, it communicates its measured value of the detected periodic function to the controller 90, not shown in FIG. 4.

The handpiece 10 of FIG. 4 includes several options. The handpiece may include a means for regulating the flow of water in the water line 116, and a means for regulating a flow of chip air in the air line 120. These means for regulating may be any of the above-discussed devices for controlling air and water regulation. In addition, a mini-controller 118 may be included in the handpiece, making the adjustable dynamic water spray system substantially self-contained, requiring merely a connection of chip air and water. Power may be provided from a separate power supply if not self-contained in the form of batteries.

Figure 5:
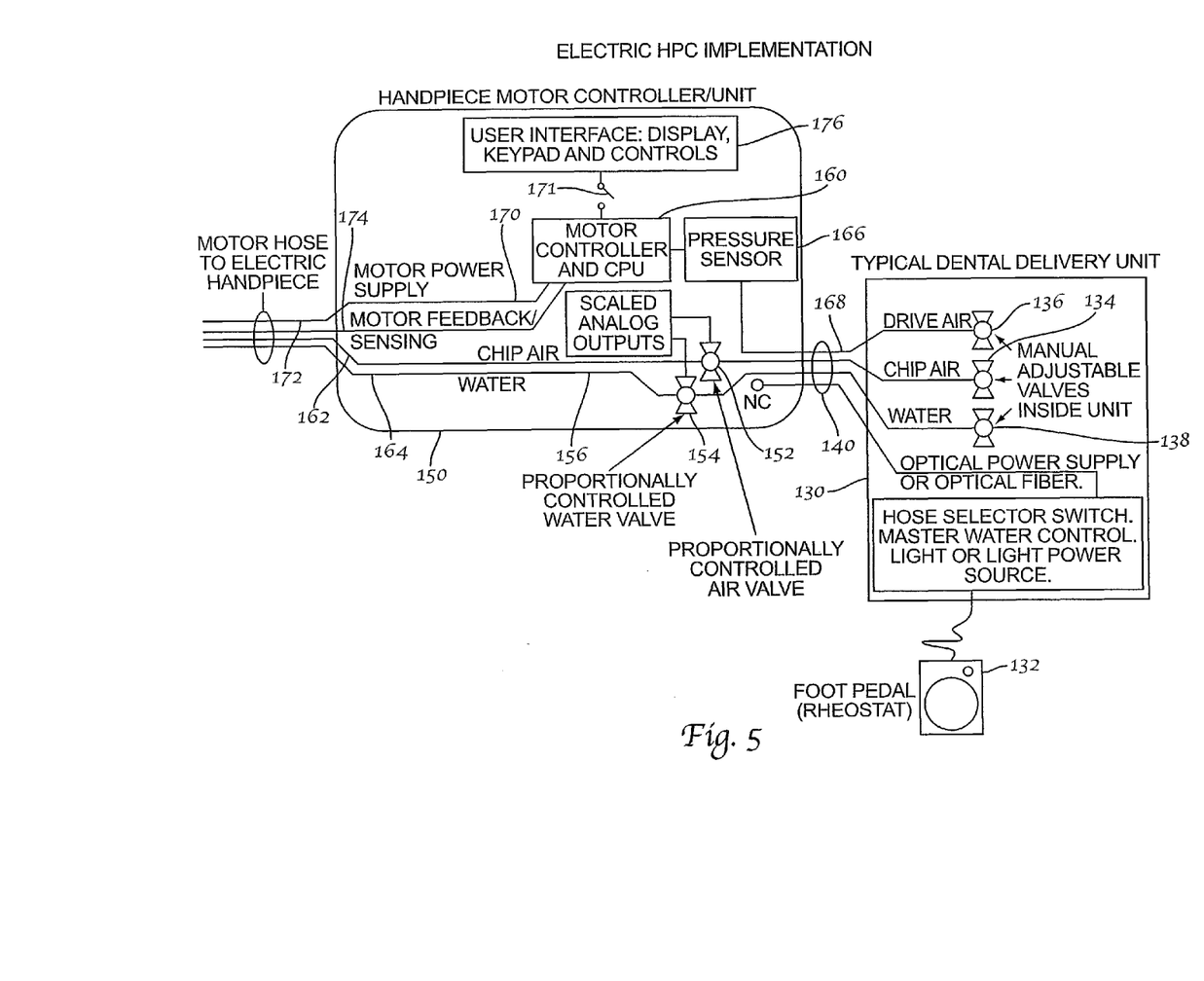
FIG. 5 depicts a schematic illustration of an adjustable dynamic water spray intensity system of the present invention configured for use with an electric handpiece.

FIG. 5 depicts a schematic illustration of an adjustable dynamic water spray intensity system of the present invention for use with an dental handpiece. FIG. 5 illustrates how the adjustable dynamic water spray unit can be used with conventional dental delivery units 130. A conventional dental unit 130 is configured to support an electric handpiece, a pneumatic handpiece or as a source for an operation dependent on light, such as curing using a specific frequency of light. A foot pedal 132 is a rheostat that is selectable to control water, light or air. The delivery unit 130 is connected with sources of that is can provide a flow of drive air, chip air, water or power. The delivery includes manually adjustable valves, a first valve 134 to control the flow of chip air, a second valve 136 to control the flow of drive air and a third valve to control the flow of water 138. Each of the valves depicted is manually adjustable, and the valves may be internal to the unit, as shown, or external to the unit. Of course, the delivery unit 130 is connected to sources of water, air and electricity. Since unit 130 is connected to support an electric handpiece, second valve is shut off in this example since no drive air is required. A connection 140 for drive air, chip air, water and power is available for connection to handpiece motor controller unit 150. Handpiece motor controller 150 is configured for use with either an electric handpiece or a pneumatic handpiece.

In the embodiment depicted in FIG. 5, handpiece motor controller 150 includes a proportionally controlled chip air valve 152 and a proportionally controlled water valve 154 in communication with scaled analog outputs 156, which in turn is connected to controller 160 that can convert the analog outputs to digital outputs as required. The proportionally controlled chip air valve 152 is located in the chip air line 162 to control chip air flow, while the proportionally controlled water valve 154 is located in the water line 164 to control water flow. A pressure sensor 166 is positioned in drive air line 168 to sense the air pressure when the handpiece motor controller 160 is used to support a pneumatic handpiece, and is in communication with the motor controller 160. In FIG., 5, the pressure sensor 166 is not active as the unit is configured to control an electric handpiece.

Motor controller 160 is configured to support either a pneumatic or an electric handpiece, with air supplied through drive air line 168 and electricity supplied from a conventional power source (not shown). Motor power supply 170 and motor feedback sensing circuit 174 that includes a sensor 70, FIGS. 2 and 3, can support either electric operation or pneumatic operation, depending on the type of handpiece used. Connections 172 coming from handpiece motor controller 160 connect to either a pneumatic or an electric handpiece. Whether the unit supports an electric handpiece or a pneumatic handpiece can be a selectable feature on user interface 176 or can be automatically determined by the controller based on feedback from the motor feedback sensing circuit 174.

In another embodiment, a controller such as the one shown in FIG. 5 can include a user selectable setting to permit the dental professional to determine whether the handpiece is responsive to a torque-related function or a measured periodic function of the tip, such as a speed-related function of the tip. This selectable setting may be actuated by the dental professional using a switch 171, as shown in FIG. 5. This is important because the controller can be programmed to respond differently to a torque-related function and to a speed-related function. When speed is used as the determining factor for controlling water flow, more water is directed at the workpiece when the cutting speed is high, and less water is directed at the workpiece when the cutting speed is low in accordance with the algorithm. This is typical for situations for light cutting, that is when the load is low. However, when torque is the determining factor for controlling water flow, more water is directed at the workpiece when the torque is high, which usually occurs as the tip slows down due to resistance to advancement. More power is being applied to the tip in these circumstances. Less water is required when torque is low, so visibility can be improved. The selection allows the dental professional to choose the mode which corresponding to the operation being performed.

In yet another embodiment, the selectable setting described above includes a setting, termed as automatic, as will become evident. A system that includes both torque-sensing capabilities and speed sensing capabilities can be configured to automatically determine based on the speed of the rotating tip and the torque encountered by the rotating tip whether speed or torque should control water flow by use of an appropriate algorithm or look-up table. Such a setting permits the dental professional to allow the controller to determine the proper setting and to actuate the switch 171. One means for detecting a function of the tip determines a characteristic of the handpiece related to tip speed, while another means for detecting a characteristic of the tip determines a characteristic of the tip related to torque and provides this data to the controller. When the controller determines that torque is low, then the controller allows the speed to control the water flow. When the controller determines that torque has increased above a predetermined level, then torque controls the flow of water directed at the workpiece regardless of the measured speed of the tip. As a further variation, of this automatic control feature, it is possible to include in the user interface 176 a feature that operates similar to a rheostat that allows the dental professional to select the torque value at which the controller determines that torque should control the water flow. This can be viewed as a partial override of the automatic feature, as the dental professional is selecting the torque override value based on the procedure being practiced, although the operation of the system is otherwise automatic. Many variations of the operation of this system by manipulation of the controller, its software or the mechanical controls and sensors that achieve the results described herein, but which are not specifically outlined for the sake of brevity, are within the scope of the present invention.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dynamic water spray intensity system comprising:
   a handpiece, the handpiece further comprising:
   a proximal end, a distal end and a body extending between the proximal end and the distal end;
   a moving tip assembled to the distal end of the handpiece;
   a means for measuring the movement of the tip,
   a means for driving the tip;
   a water line in the body extending from the proximal end to the distal end;
   an air line in the body extending from the proximal end to the distal end and combining with the water line to provide a water spray to a workpiece positioned in proximity to the rotating tip;
   a water supply;
   a water conduit connected to the water line at the proximal end of the handpiece;
   an air supply;
   an air conduit connected to the air line at the proximal end of the handpiece;
   a means for comparing the flow of water through the handpiece directly with the movement of the tip; and
   a means for regulating the flow of water to the workpiece based directly on the measured movement of the tip.

2. The dynamic water spray intensity of claim 1 wherein the measured movement of the tip is a rotational speed.

3. The dynamic water spray intensity system of claim 1 wherein the means for driving the tip in the handpiece is an electric motor.

4. The dynamic water spray intensity system of claim 1 wherein the means for driving the tip in the handpiece is an air turbine connected to an air supply, the handpiece further including a second air line extending from the proximal end to the air turbine.

5. The dynamic water spray intensity system of claim 4 further including an air supply in communication with the second air line to drive the turbine.

6. The dynamic water spray intensity system of claim 1 wherein the means for measuring the movement of the tip is a sensor.

7. The dynamic water spray intensity system of claim 6 wherein the sensor for measuring movement of the tip is an accelerometer.

8. The dynamic water spray intensity system of claim 7 wherein the means for driving the tip further includes bearings, the movement of the tip is a periodic vibration of the bearings and wherein the accelerometer measures the periodic vibration of the bearings.

9. The dynamic water spray intensity system of claim 3 wherein the means for measuring the rotational speed of the tip is a measurement of the current drawn by the electric motor.

10. The dynamic water spray intensity system of claim 1 wherein the means for comparing the flow of water directly with the measured movement of the tip further includes a controller in communication with the means for measuring the movement of the tip, the controller further in communication with the means for regulating water flow, the controller including an algorithm that determines water flow as a function of tip movement, the controller signaling the means for regulating the water flow as required to maintain the water flow consistent with tip movement.

11. The dynamic water spray intensity system of claim 9 wherein the means for regulating water flow is a solenoid valve operable in response to communication from the controller.

12. The dynamic water spray intensity system of claim 1 further including a means for measuring the flow of water to the handpiece, and wherein the means for comparing the flow of water through the handpiece with the tip movement is a controller in communication with the means for measuring the tip movement and the means for measuring the flow of water to the handpiece, the controller including an algorithm that determines water flow directly as a function of measured tip movement, compares the measured water flow with the measured tip movement, the controller further in communication with the means for regulating the water flow as required to maintain the water flow consistent with tip movement.

13. The dynamic water spray intensity system of claim 10 wherein the means for measuring the flow of water further includes a flow sensor.

14. The dynamic water spray intensity system of claim 1 wherein the means for regulating the flow of water to the handpiece is a variable flow valve.

15. The dynamic water spray intensity system of claim 14 wherein the variable valve is controllable by and in communication with the controller, the valve responsive to a signal from the controller to modify the flow of water in the conduit to maintain the measured water flow consistent with the tip movement.

16. The dynamic water spray intensity system of claim 14 wherein the controller further includes an algorithm, wherein the algorithm compares the measured tip movement with the measured flow of water to determine whether the flow of water requires an adjustment, the controller further in communication with the variable valve, wherein the controller signals the valve as required to modify the water flow based on the algorithmic determination.

17. The dynamic water spray intensity system of claim 9 wherein the system further includes a means for determining the flow of air in the air line combined with the water line, the controller including an algorithm that compares the flow of air with at least one of the flow of water and the tip movement.

18. The dynamic water spray intensity system of claim 1 wherein the means for regulating the flow of water to the workpiece is based solely on the measured speed of the tip.

19. The dynamic water spray intensity system of claim 1 wherein the measured movement of the tip is a linear movement.

20. A dental handpiece comprising:
a proximal end, a distal end and a body extending between the proximal end and the distal end;
a rotating tip assembled to the distal end of the handpiece;
a means for driving the rotating tip;
a means for measuring a periodic function of the tip,
a water line in the body extending from the proximal end to the distal end;
an air line in the body extending from the proximal end to the distal end and combining. with the water line to provide a water spray to a workpiece positioned in proximity to the rotating tip wherein the means for driving the rotating tip includes bearings,
wherein the means for measuring the periodic function of the tip is an accelerometer, wherein the accelerometer directly measures a periodic vibration of the bearings; and
wherein the measured periodic vibration of the bearings regulates water flow in the water line.

21. The dental handpiece of claim 20 wherein the means for measuring the periodic function of the tip is a sensor.

22. The dental handpiece of claim 21 wherein the sensor is an accelerometer.

23. The dental handpiece of claim 20 further including a means for regulating a flow of water in the water line.

24. The dental handpiece of claim 23 further including a controller that controls the means for regulating the flow of water in the water line as a function of the measured periodic vibration of the bearings.

25. The dental handpiece of claim 24 further including a means for regulating a flow of air in the air line that combines with water from the water line producing chip air.

26. The dental handpiece of claim 25 wherein the controller further controls the means for regulating the flow of air in the air line as a function of at least one of the flow of water in the water line and the measured periodic function of the handpiece.

27. A dynamic water spray intensity system comprising:
a handpiece further comprising
a proximal end, a distal end and a body extending between the proximal end and
the distal end;
a rotatable air turbine powered by compressed air located at the distal end of the handpiece, the air turbine further including a set of bearings,
a chuck attached to the air turbine for removably inserting a rotating tip;

a sensor for detecting the rotating tip speed of an assembled tip;
a water line in the body extending between the proximal end and the distal end;
a first air line in the body extending from the proximal end to the distal end and combining with the water line to provide a water spray to a workpiece positioned in proximity to the assembled tip;
a second air line in the body extending from the proximal end to the rotatable air turbine;
a water supply;
a conduit connected to the proximal end of the handpiece to provide water from the water supply to the handpiece to provide a flow of water to a workpiece positioned in proximity to the rotating tip;
a means for determining the flow of water through the conduit;
a means for comparing the flow of water through the conduit directly with the rotating speed of the tip;
a means for regulating the flow of water through the conduit based on the detected speed of the rotating tip;
a supply of pressurized air in communication with the proximal end of the handpiece to provide pressurized air to the first air line and the second air line; and
means for regulating the flow of air to the second air line.

28. The dental handpiece of claim 27 wherein the means for determining the flow of water through the conduit is a flow sensor.

29. The dynamic water spray intensity system of claim 27 wherein the means for regulating the flow of water through the conduit based on the detected speed of the rotating tip is a solenoid valve controllable in response to a signal from the sensor indicative of measured tip speed.

30. The dynamic water spray intensity system of claim 27 wherein the means for regulating the flow of water through the conduit based on the detected rotating speed of the tip is determined by an amount of pressurized air provided from air supply to the air turbine through the second supply line.

31. The dynamic water spray intensity system of claim 27 further including a means for regulating the flow of air to provide the water spray, wherein the means for regulating the flow of air to provide the water spray is determined by an amount of pressurized air provided from the air supply to the air turbine through the second supply line.

32. The dynamic water spray intensity system of claim 30 further including a means for regulating the flow of air to provide the water spray, wherein the flow of air is determined by water through the conduit, and the means for regulating the flow of air to provide the water spray is determined by the amount of water flow through the means for regulating the flow of water through the conduit.

33. The dynamic water spray system of claim 27 wherein the means for comparing the flow of water through the handpiece with the means for measuring the rotating speed of the tip is a controller.

34. The dynamic water spray system of claim 33 wherein the controller includes a microprocessor.

35. The dynamic water spray system of claim 33 wherein the means for regulating the flow or air to the second line is a solenoid valve controllable in response to a signal.

36. The dynamic water spray system of claim 35 wherein the controller is in communication with the sensor for detecting the rotating tip speed, the controller further directly comparing the flow of water through the handpiece with the detected rotating tip speed, the controller further signaling the means for regulating the flow of water through the handpiece to adjust the flow of water as required based on the detected rotating tip speed.

37. The dynamic water spray system of claim 36 further including a controllable valve to regulate the flow of air to provide the water spray, the controller further signaling the valve to adjust the flow of air to provide the water spray as required based on one of the flow of water and the detected rotating tip speed.

38. A dynamic water spray intensity system comprising:
a handpiece further comprising
a proximal end, a distal end and a body extending between the proximal end and the distal end;
an electric motor positioned in the handpiece;
a set of bearings and a chuck for removably inserting a rotating tip rotated by the electric motor;
a sensor for detecting the rotating tip speed of an assembled tip;
a water line in the body extending between the proximal end and the distal end;
an air line in the body extending from the proximal end to the distal end and combining with the water line to provide a water spray to a workpiece positioned in proximity to the assembled tip;
a water supply;
a conduit connected to the proximal end of the handpiece to provide water from the water supply to the handpiece to provide a flow of water to a workpiece positioned in proximity to the rotating tip;
a means for comparing the flow of water through the conduit directly with the detected rotating tip speed;
a means for regulating the flow of water through the conduit based on the detected rotating tip speed;
a supply of pressurized air in communication with the proximal end of the handpiece to provide pressurized air to the air line; and
a source of electricity to power the electric motor.

39. The dynamic water spray intensity system of claim 38 further including a means for determining the flow of water through the conduit.

40. The dynamic water spray intensity system of claim 39 wherein the means for determining the flow of water through the conduit is a flow sensor.

41. The dynamic water spray intensity system of claim 38 wherein the means for regulating the flow of water through the conduit based on the rotating tip speed is a solenoid valve controllable in response to a signal from the sensor indicative of measured tip speed.

42. A dynamic water spray intensity system comprising:
a handpiece further comprising
a proximal end, a distal end, and a body extending between the proximal end the distal end;
an electric motor positioned in the handpiece for providing power;
a rotating tip extending from the distal end of the handpiece powered by the electric motor;
a set of bearings and a chuck for removably inserting a rotating tip rotated by the electric motor;
a sensor for detecting a periodic function of the tip indicative of the rotating tip speed;
a water line in the body extending between the proximal end and the distal end;
an air line in the body extending from the proximal end to the distal end and combining with the water line to provide a water spray to a workpiece positioned in proximity to the assembled tip;

a water supply in communication with the water line to provide a flow of water to a workpiece positioned in proximity to the rotating tip;

means for determining the flow of water through the handpiece;

means for comparing the flow of water through the handpiece with the rotating speed of the tip;

means for regulating the flow of water through the handpiece; and a controller in communication with the sensor for detecting the periodic function of the handpiece and with the means for regulating the flow of water, wherein the controller adjusts the means for regulating the flow of water through the handpiece to meter fluid to the handpiece when the means for comparing the flow of water through the handpiece indicates that the flow of water requires adjustment based on the detected rotating tip speed.

43. The dynamic water spray intensity system of claim 42 wherein the means for comparing the flow of water through the handpiece is accomplished by the controller, wherein the controller receives a signal from the sensor for detecting the periodic function, calculates the rotational speed of the tip, compares the calculated speed to a preset speed range, determines the water flow requirements for the preset speed range and adjusts the means for regulating the flow of water as required.

44. The dynamic water spray intensity system of claim 42 wherein the means for determining the flow of water through the handpiece is a flow sensor.

45. The dynamic water spray intensity system of claim 42 wherein the means for determining the flow of water through the handpiece is a mass flow meter.

46. The dynamic water spray intensity system of claim 42 wherein the means for regulating the flow of water through the handpiece is a valve.

47. The dynamic water spray intensity system of claim 46 wherein the valve for regulating the flow of water through the handpiece is a solenoid valve.

48. The dynamic water spray intensity system of claim 42 wherein the handpiece further including an air turbine.

49. The dynamic water spray intensity system of claim 48 wherein the means for providing power to the handpiece includes a source of pressurized air connected to drive the gas turbine.

50. The dynamic water spray intensity system of claim 42 wherein the handpiece further including an electric motor.

51. The dynamic water spray intensity system of claim 50 wherein the means for providing power to the handpiece includes a source of electricity connected to the electric motor.

52. A dynamic water spray intensity system, comprising:
a dental handpiece comprising
a proximal end, a distal end and a body extending between the proximal end and the distal end;
a rotating tip assembled to the distal end of the handpiece;
a means for driving the rotating tip;
a water conduit in the body extending from the proximal end to the distal end;
an air line in the body extending from the proximal end to the distal end and combining with the water conduit to provide a water spray to a workpiece positioned in proximity to the rotating tip;
a means for measuring a flow of water through the water conduit;
a means for measuring a periodic function of the tip;

a means for determining the torque encountered by the rotating tip;
a means for comparing the flow of water through the conduit with the torque encountered by the rotating tip;
a means for regulating the flow of water to the workpiece based on the torque encountered by the rotating tip;
a means for comparing the flow of water through the conduit directly with the measured periodic function of the rotating tip;
a means for regulating the flow of water to the workpiece based on the measured periodic function of the tip; and
a switch selectable between regulating the flow of water to the workpiece based on the torque encountered by the rotating tip and regulating the flow of water to the workpiece based on the directly measured periodic function of the tip.

53. The dynamic water spray intensity system of claim 52 wherein the means for comparing the flow of water through the conduit with the torque encountered by the rotating tip and the means for comparing the flow of water through the conduit with the measured periodic function of the tip is a controller.

54. The dynamic water spray intensity system of claim 53 wherein the means for measuring the periodic function of the rotating tip is a sensor.

55. The dynamic water spray intensity system of claim 54 wherein the sensor is an accelerometer.

56. The dynamic water spray system of claim 53 wherein the means for regulating the flow of water to the workpiece is a solenoid valve in communication with the controller, the controller comparing the measured periodic function of the rotating tip with the measured flow of water through the conduit and signaling the solenoid valve to adjust the flow of water as required based on the measured periodic function of the rotating tip.

57. The dynamic water spray system of claim 53 wherein the means for measuring the flow of water through the conduit is selected from the group consisting of a sensor and a mass flow meter.

58. The dynamic water spray intensity system of claim 53 wherein the means for measuring the flow of water is a signal from the regulator indicative of the regulator opening.

59. The dynamic water spray intensity system of claim 53 wherein the means for driving the rotating tip is an electric motor and wherein the means for determining the torque encountered by the rotating tip is an ammeter to measure the current drawn by the motor, the ammeter in communication with the controller.

60. The dynamic water spray intensity system of claim 53 wherein the means for driving the rotating tip is an air turbine, an air supply and a means for supplying air to the air turbine at a preselected pressure, the means for supplying air at a preselected pressure being in communication with the controller, and wherein controller determines the torque encountered by the rotating tip as a function of the preselected air pressure and the speed of the rotating tip.

61. The dynamic water spray intensity system of claim 60 wherein the means for supplying air to the air turbine at a preselected pressure is an air supply in fluid communication with the handpiece and an air regulator in communication with the controller.

62. The dynamic water spray intensity system of claim 60 wherein the means for supplying air to the air turbine at a preselected pressure is an air supply in fluid communication with the handpiece, an air valve for controlling the flow of air to the handpiece and a sensor in communication with the controller for measuring the flow of air to the handpiece.

63. A dynamic water spray intensity system, comprising:
a dental handpiece comprising
- a proximal end, a distal end and a body extending between the proximal end and the distal end;
- a rotating tip assembled to the distal end of the handpiece;
- a means for driving the rotating tip;
- a water conduit in the body extending from the proximal end to the distal end;
- an air line in the body extending from the proximal end to the distal end and combining with the water conduit to provide a water spray to a workpiece positioned in proximity to the rotating tip;

a means for controlling a flow of water through the water conduit;
a means for measuring a periodic function of the tip;
a means for determining the torque encountered by the rotating tip;
a controller for comparing the flow of water through the conduit directly with the measured periodic function of the rotating tip and further determining the flow of water through the water conduit based on the measured periodic function of the rotating tip, the controller further in communication with the means for controlling the flow of water through the water conduit; and
wherein the measured periodic function of the rotating tip is a periodic motion of the rotating tip or a speed of the rotating tip.

64. The dynamic water intensity system of claim 63 wherein the means for controlling the flow of water further including a means for determining the flow of water through the water conduit in communication with the controller, and a regulator for controlling water flow through the conduit operable in response to a communication from the controller.

65. The dynamic water intensity system of claim 64 wherein the means for determining the flow of water through the conduit is in communication with the controller and is selected from the group consisting of a mass flow meter and a sensor.

66. The dynamic water spray intensity system of claim 63 wherein the means for measuring the periodic function of the rotating tip is a speed sensor.

67. The dynamic water spray intensity system of claim 66 wherein the sensor is an accelerometer.

68. The dynamic water spray system of claim 63 wherein the means for controlling the flow of water is a signal from a regulator indicative of the regulator opening.

69. The dynamic water spray intensity system of claim 63 wherein the means for driving the rotating tip is an electric motor, wherein the means for determining the torque encountered by the rotating tip is an ammeter to measure the current drawn by the motor, the ammeter in communication with the controller and wherein the means for determining the periodic function of the tip is a speed sensor.

* * * * *